(12) United States Patent
McIntire et al.

(10) Patent No.: US 8,251,736 B2
(45) Date of Patent: Aug. 28, 2012

(54) CONNECTOR ASSEMBLY FOR CONNECTING AN ELECTRICAL LEAD TO AN ELECTRODE

(75) Inventors: James F. McIntire, West Linn, OR (US); Brian Erik Haug, Portland, OR (US)

(73) Assignee: Tyco Electronics Corporation, Berwyn, PA (US)

( * ) Notice: Subject to any disclaimer, the term of this patent is extended or adjusted under 35 U.S.C. 154(b) by 79 days.

(21) Appl. No.: 12/236,333

(22) Filed: Sep. 23, 2008

(65) Prior Publication Data

US 2010/0075527 A1 Mar. 25, 2010

(51) Int. Cl.
*H01R 13/627* (2006.01)

(52) U.S. Cl. ...................................... 439/357

(58) Field of Classification Search ............... 439/357, 439/345, 496, 411, 77, 495, 353, 859, 592, 439/17, 20
See application file for complete search history.

(56) References Cited

U.S. PATENT DOCUMENTS

| | | |
|---|---|---|
| 3,069,753 A | 12/1962 | Lalmond et al. |
| 3,325,769 A | 6/1967 | Travis |
| 3,353,141 A | 11/1967 | Budai |
| 3,462,542 A | 8/1969 | Richter |
| 3,513,045 A | 5/1970 | Emmel et al. |
| 3,599,629 A | 8/1971 | Gordy |
| 3,641,482 A | 2/1972 | Bretting |
| 3,670,290 A | 6/1972 | Angele et al. |
| 3,696,319 A | 10/1972 | Olsson |
| 3,802,974 A | 4/1974 | Emmel |
| 4,112,941 A | 9/1978 | Larimore |
| 4,331,153 A | 5/1982 | Healy |
| 4,350,165 A | 9/1982 | Striese |
| 4,353,372 A | 10/1982 | Ayer |
| 4,357,750 A | 11/1982 | Ostman |
| 4,438,999 A | 3/1984 | Lang |
| 4,487,992 A | 12/1984 | Tomita |
| 4,490,005 A | 12/1984 | Hovey |
| 4,573,752 A | 3/1986 | Rich |

(Continued)

FOREIGN PATENT DOCUMENTS

EP 1264575 A2 12/2002

OTHER PUBLICATIONS

International Search Report for International Application No. PCT/US2009/005175, mailed Dec. 18, 2009.

(Continued)

*Primary Examiner* — Jean F Duverne (57) ABSTRACT

A connector assembly is provided for connecting an electrical lead to the electrical contact of an electrode. The connector assembly includes a retention plate having an opening configured to receive the electrical contact of the electrode therethrough such that the retention plate is held on the electrode, and a housing including a body and a receptacle extending into the body. The receptacle includes a size and shape that is complimentarily to the electrical contact of the electrode such that the receptacle is configured to receive at least a portion of the electrical contact therein. The receptacle is configured such that when the electrical contact is received within the receptacle, the receptacle is configured to hold a portion of the electrical lead within the receptacle between the electrical contact and the body of the housing such that the electrical lead is engaged with and electrically connected to the electrical contact. A connection member is configured to hold the housing on the retention plate.

20 Claims, 10 Drawing Sheets

U.S. PATENT DOCUMENTS

| | | | |
|---|---|---|---|
| 4,653,501 A | | 3/1987 | Cartmell et al. |
| 4,686,995 A | * | 8/1987 | Fournial et al. ............... 600/391 |
| 4,757,817 A | | 7/1988 | Healy |
| 4,945,911 A | | 8/1990 | Cohen et al. |
| 5,212,348 A | | 5/1993 | Gibson |
| 5,232,383 A | | 8/1993 | Barnick |
| 5,235,132 A | | 8/1993 | Ainsworth et al. |
| 5,250,127 A | | 10/1993 | Hara |
| 5,645,440 A | | 7/1997 | Tobler et al. |
| 5,897,406 A | | 4/1999 | Benes |
| 5,978,693 A | | 11/1999 | Hamilton et al. |
| 6,071,141 A | | 6/2000 | Semmeling et al. |
| 6,531,658 B2 | | 3/2003 | Tanaka et al. |
| 6,659,794 B2 | | 12/2003 | Yamatani et al. |
| 6,672,788 B2 | | 1/2004 | Hathaway |
| 6,705,899 B1 | | 3/2004 | Ji |
| 6,766,578 B1 | | 7/2004 | Swanson et al. |
| 6,847,836 B1 | | 1/2005 | Sujdak |
| 6,979,224 B2 | | 12/2005 | Boemmel et al. |
| 7,001,207 B2 | | 2/2006 | Boemmel et al. |
| 7,062,309 B2 | * | 6/2006 | Ryu et al. ...................... 600/372 |
| 7,172,455 B2 | | 2/2007 | Pabst et al. |
| 7,297,872 B2 | | 11/2007 | Morijiri |
| 7,510,425 B2 | | 3/2009 | Kuo et al. |
| 7,520,774 B2 | | 4/2009 | Watanabe |
| 7,521,634 B2 | | 4/2009 | Clem et al. |
| 7,538,276 B2 | | 5/2009 | Narumi |
| 2005/0251004 A1 | | 11/2005 | Istvan et al. |
| 2007/0175652 A1 | | 8/2007 | Narumi |

OTHER PUBLICATIONS

International Search Report for International Application No. PCT/US2009/005173, mailed Nov. 26, 2009.

International Search Report for International Application No. PCT/US2009/005170, mailed Nov. 10, 2009.

* cited by examiner

CONNECTOR ASSEMBLY FOR CONNECTING AN ELECTRICAL LEAD TO AN ELECTRODE

BACKGROUND OF THE INVENTION

The subject matter described and illustrated herein relates generally to electrical lead assemblies, and more particularly, to a connector assembly for connecting an electrical lead to an electrode.

An electrocardiograph (ECG) system monitors heart electrical activity in a patient. Conventional ECG systems utilize electrodes placed on a patient in specific locations to detect electrical impulses generated by the heart during each beat. Typically, the electrical impulses or signals are detected by and directly transferred from the electrodes to a stationary ECG monitor via multiple cables or wires. The ECG monitor performs various signal processing and computational operations to convert the raw electrical signals into meaningful information that can be displayed on a monitor or printed out for review by a physician.

ECG measurements are taken by applying electrodes to different chest locations and additional body locations, such as the arms and legs. Each of the electrodes is electrically connected to the ECG monitor by a corresponding electrical lead. To electrically connect the electrical leads to the electrodes, an end portion of each electrical lead typically includes an electrical connector that engages an electrical contact, for example a stud, of the corresponding electrode. Each electrical connector is typically connected to the corresponding lead using conventional methods, such as by welding, soldering, or crimping the electrical connector to the end portion of the corresponding electrical lead. However, connecting the electrical connectors to the electrical leads may increase the cost and/or difficulty of manufacturing and/or assembling the electrical leads. Moreover, the electrical connectors typically engage the electrical contacts of the electrodes using a "snap", "pinch", or "grabber" arrangement, which may increase a size and/or a complexity of the electrical leads and therefore may increase the cost and/or difficulty of manufacturing the electrical leads, assembling the electrical leads, and/or connecting the electrical leads to the electrodes.

There is a need for an electrical lead that is less costly and/or more easily manufactured, assembled, and/or connected to an electrode than at least some known electrical leads.

BRIEF DESCRIPTION OF THE INVENTION

In one embodiment, a connector assembly is provided for connecting an electrical lead to the electrical contact of an electrode. The connector assembly includes a retention plate having an opening configured to receive the electrical contact of the electrode therethrough such that the retention plate is held on the electrode, and a housing including a body and a receptacle extending into the body. The receptacle includes a size and shape that is complimentarily to the electrical contact of the electrode such that the receptacle is configured to receive at least a portion of the electrical contact therein. The receptacle is configured such that when the electrical contact is received within the receptacle, the receptacle is configured to hold a portion of the electrical lead within the receptacle between the electrical contact and the body of the housing such that the electrical lead is engaged with and electrically connected to the electrical contact. A connection member is configured to hold the housing on the retention plate.

In another embodiment, an electrical lead assembly is provided for connection to an electrical contact of an electrode. The electrical lead assembly includes a retention plate having an opening configured to receive the electrical contact of the electrode therethrough such that the retention plate is held on the electrode, and a housing including a body and a receptacle extending into the body. The receptacle is configured to receive at least a portion of the electrical contact therein. The electrical lead assembly also includes an electrical lead having an end portion. A connection member holds the housing on the retention plate. The receptacle is configured such that when the electrical contact is received within the opening of the retention plate and within the receptacle, a portion of the end portion of the electrical lead is held within the receptacle between the electrical contact of the electrode and the body of the housing such that the electrical lead is engaged with and electrically connected to the electrical contact.

In another embodiment, an electrode lead assembly is provided. The electrode lead assembly includes an electrode including an electrical contact, and a retention plate held on the electrode. The retention plate includes an opening having the electrical contact of the electrode received therethrough. A housing includes a body and a receptacle extending into the body. At least a portion of the electrical contact is received into the receptacle. An electrical lead has an end portion. At least a portion of the end portion of the electrical lead is held within the receptacle between the electrical contact of the electrode and the body of the housing such that the electrical lead is engaged with and electrically connected to the electrical contact. A connection member holds the housing on the retention plate.

BRIEF DESCRIPTION OF THE DRAWINGS

FIG. 6 is a schematic diagram of an exemplary embodiment of an electrocardiogram (ECG) system that the electrode lead set shown in FIG. 1 may be used with.

DETAILED DESCRIPTION OF THE INVENTION

Figure 1:
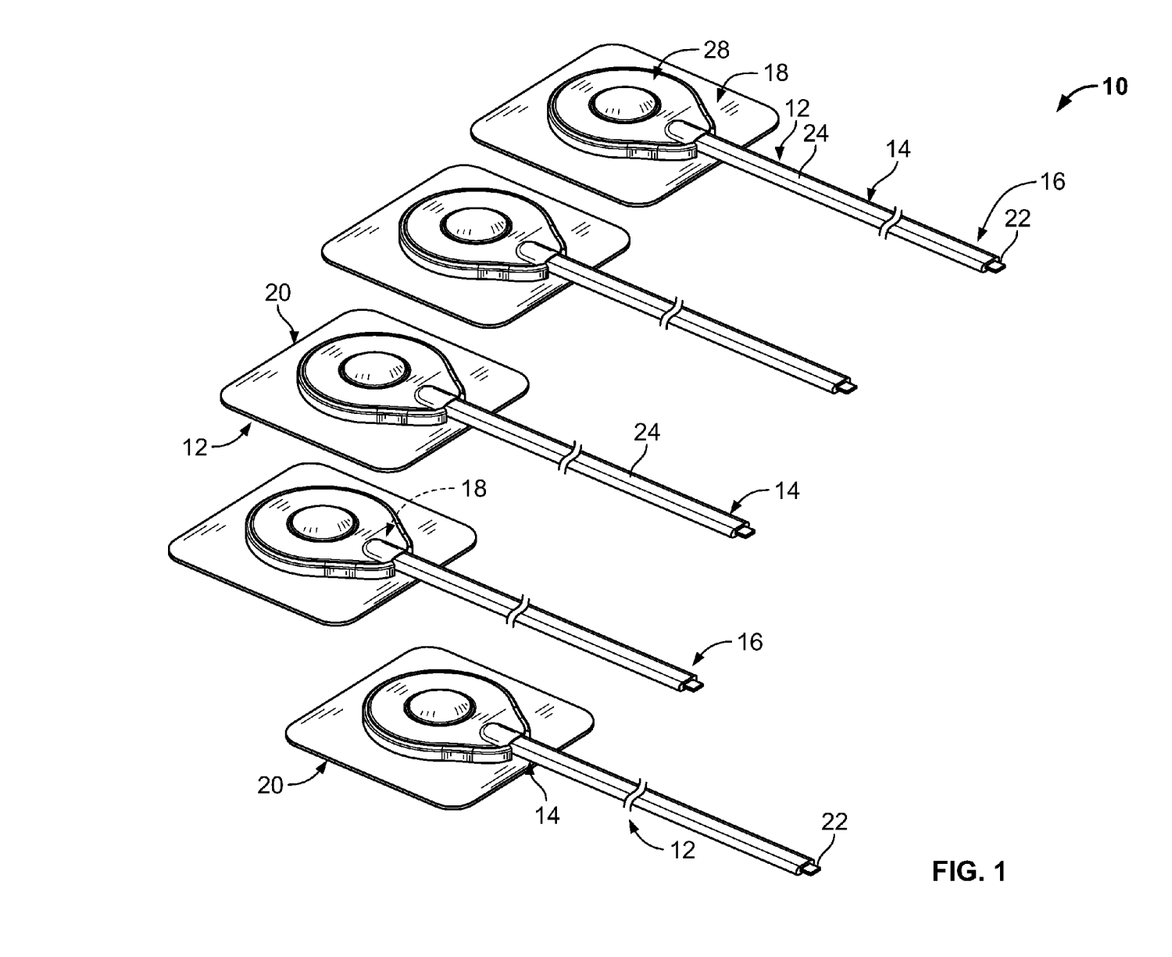
FIG. 1 is a perspective view of an exemplary embodiment of an electrode lead set for electrical connection to a patient's body.

FIG. 1 is a perspective view of an exemplary embodiment of an electrode lead set 10 for electrical connection to a patient's body. The electrode lead set 10 includes a plurality of electrode lead assemblies 12. Each electrode lead assembly 12 includes an electrical lead 14 that extends along a length from a proximal end portion 16 to a distal end portion 18. The distal end portion 18 of each of the electrical leads 14 includes an electrode 20. Specifically, and as will be described in more detail below, each electrode 20 is electrically connected to the corresponding electrical lead 14 at the distal end portion 18 thereof. The electrodes 20 are each configured to be placed at different locations on the patient's body for measuring physiological information of the patient's body. As will be described in more detail below, connector assemblies 28 are provided for connecting the electrical leads 14 to the corresponding electrodes 20.

Each electrical lead 14 includes an electrical conductor 22 that extends along the length of the electrical lead 14 between the proximal and distal end portions 16 and 18, respectively. Each of the electrical conductors 22 is electrically connected to the corresponding electrode 20 to provide an electrical connection between the electrode 20 and any electronic device, for example any electronic device that reads and/or delivers electrical signals from and/or to a body, such as, but not limited to, a monitoring device (such as, but not limited to, an electrocardiogram (ECG) monitoring device (e.g., the ECG monitoring device 102 shown in FIG. 6), a hand-held system monitor (not shown), and/or the like), a stimulating device, and/or the like. Specifically, at the proximal end portion 16 of each of the electrical leads 14, the electrical conductor 22 is electrically connected to the electronic device (whether directly or indirectly using an extension, one or more electrical connectors, and/or the like) such that each of the electrodes 20 are electrically connected to one or more corresponding circuits (not shown) of the electronic device. The electronic device may be any suitable processing device that is capable of performing signal processing and computational operations to convert the raw electrical signals from and/or to the electrodes 20 into meaningful information (such as, but not limited to, ECG information and/or the like) that may optionally be displayed on a monitor (e.g., the monitor 104 shown in FIG. 6), printed for review by a physician, and/or the like.

In the exemplary embodiment, each of the electrical leads 14 includes the electrical conductor 22 and an electrically insulative cover 24. In other embodiments, each of the electrical leads 14 may be shielded along at least a portion of the length of the electrical lead 14. The electrical leads 14 may be shielded using any suitable arrangement, configuration, structure, means, and/or the like, such as, but not limited to, surrounding at least a portion of the electrical conductors 22 with any suitable electrically insulative material(s) (not shown), and surrounding at least a portion of the insulative material with an electrically conductive material (not shown) that is at least partially surrounded by the electrically insulative cover 24.

The electrical conductors 22 may each be fabricated from any suitable electrically conductive material(s) that enables the electrical conductors 22 to electrically connect the electrodes 20 to the electronic device and/or that enables the electrode lead set 10 to function as described herein, such as, but not limited to, silver, aluminum, gold, copper, other metallic conductors, non-metallic conductors (such as, but not limited to, carbon and/or the like), and/or the like. The electrical conductors 22 may also have any suitable configuration, shape, and/or the like that that enables the electrical conductors 22 to electrically connect the electrodes 20 to the electronic device and/or that enables the electrode lead set 10 to function as described herein, such as, but not limited to, an approximately cylindrical wire (whether the wire consists of a plurality of strands or only one strand), an approximately planar shape, and/or the like. The insulative cover 24 may be fabricated from any suitable insulative material(s) that facilitates insulating the electrical conductors 22 and/or that enables the electrode lead set 10 to function as described herein, such as, but not limited to, polyester (e.g., Mylar®), polyvinyl chloride, thermo-plastic-elastomer, and/or polyimide (e.g., Kapton®)).

The electrode lead set 10 may include any number of electrode lead assemblies 12 for positioning any number of electrodes 20 at any number of locations on the patient's body. In the exemplary embodiment of FIGS. 1 and 6, the electrode lead set 10 includes five electrode lead assemblies 12 for use within an ECG system (e.g., the ECG system 100 shown in FIG. 6). For example, the electrodes 20 of four of the five electrode lead assemblies 12 are configured to be placed at different limbs of a patient's body (e.g., both arms and both legs) and one of the five electrode lead assemblies 12 is configured to be placed on the chest region of the patient's body. An example of an alternative embodiment of the electrode lead set 10 includes only three electrode lead assemblies 12 for use within an ECG system, wherein the electrodes 20 of the three electrode lead assemblies 12 are configured to be placed at different limbs of the patient's body (e.g., both arms and the left leg). Yet another example of an alternative embodiment of the electrode lead set 10 includes ten electrode lead assemblies 12 wherein the electrodes 20 of six of the electrode lead assemblies 12 are configured to be placed at six different locations on a chest region of the patient's body (e.g., the prescribed ECG precordial locations $V_1$, $V_2$, $V_3$, $V_4$, $V_5$, and $V_6$ of the American Heart Association (AHA) or the prescribed ECG precordial locations $C_1$, $C_2$, $C_3$, $C_4$, $C_5$, and $C_6$ of the International Electrotechnical Commission (IEC)) and the electrodes 20 of four electrode lead assemblies 12 are configured to be placed on different limbs of the patient's body (e.g., the prescribed locations RA, LA, RL, and LL of the AHA or the prescribed locations R, L, N, and F of the IEC). Even another example of an alternative embodiment of the electrode lead set 10 includes twelve electrode lead assemblies 12 for use within an ECG system, wherein some of the electrodes 20 of the twelve electrode lead assemblies 12 are configured to be placed at different limbs of the patient's body and some of the electrodes 20 of the twelve electrode lead assemblies 12 are configured to be placed on the chest region of the patient's body. The electrode lead set 10 is not limited to the three, five, ten, and twelve electrode lead assembly 12 embodiments described and/or illustrated herein, but rather may include any number of electrode lead assemblies 12 for positioning any number of electrodes 20 at any number of locations on the patient's body.

Figure 2:
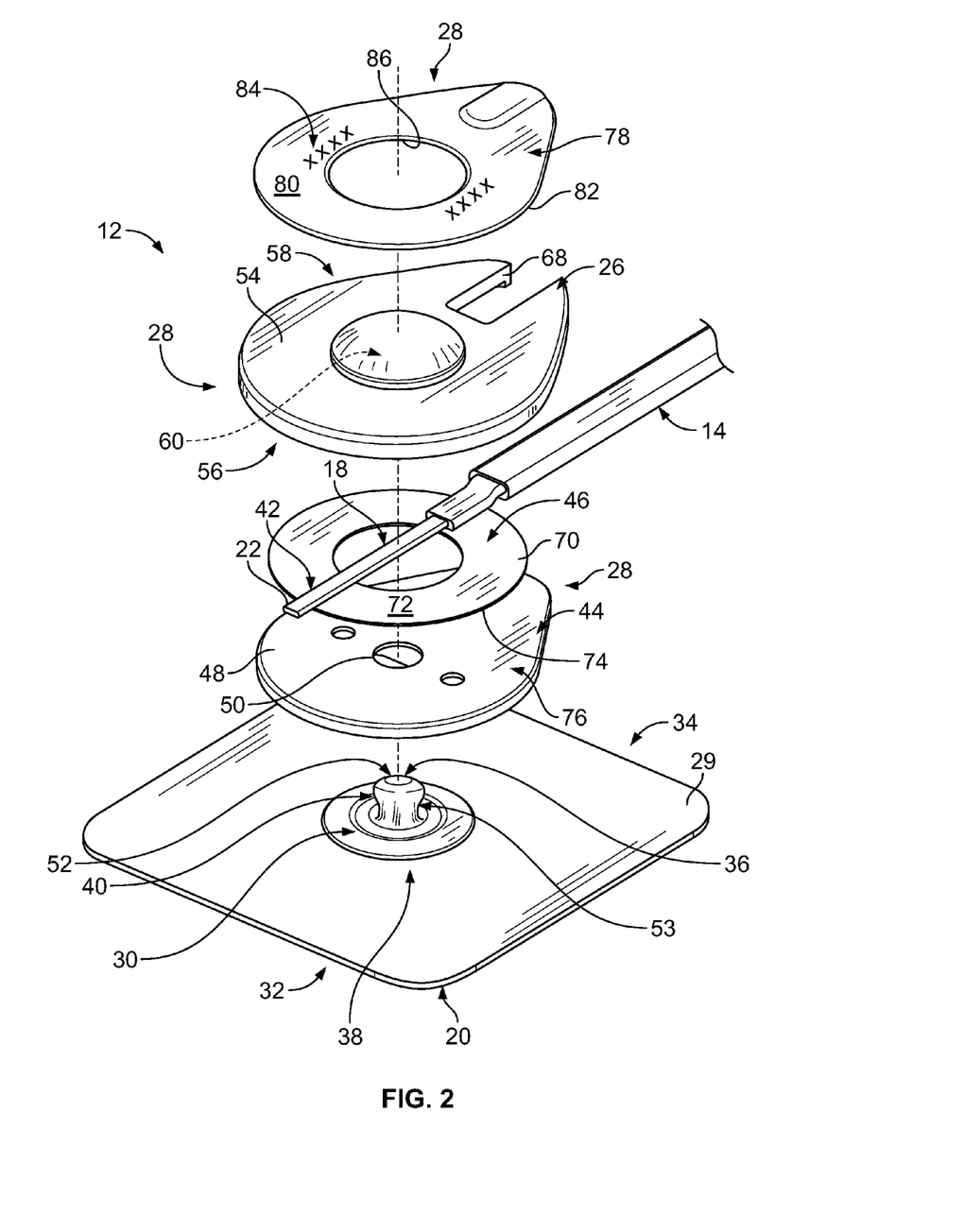
FIG. 2 is a partially exploded perspective view of a portion of an exemplary embodiment of an electrode lead assembly of the electrode lead set shown in FIG. 1.
Figure 3:
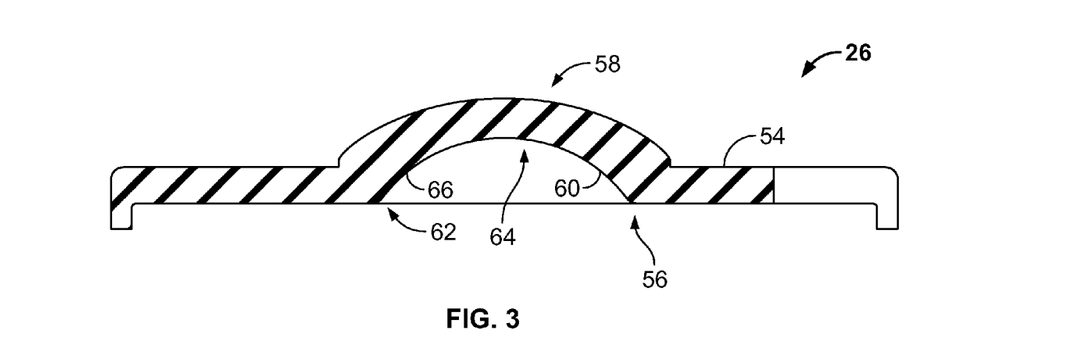
FIG. 3 is a cross-sectional view of an exemplary embodiment of a housing of a connector assembly of the electrode lead assembly shown in FIG. 2.

FIG. 2 is an exploded perspective view of a portion of an exemplary embodiment of an electrode lead assembly 12 of the electrode lead set 10 (FIG. 1). FIG. 3 is a cross-sectional view of an exemplary embodiment of a housing 26 of a connector assembly 28 of the electrode lead assembly 12 (FIGS. 1 and 2). Each electrode lead assembly 12 includes the electrical lead 14, the electrode 20, and the connector assembly 28. A combination of an electrical lead 14 and the connector assembly 28 may be referred to herein as an "electrical lead assembly".

Figure 5:
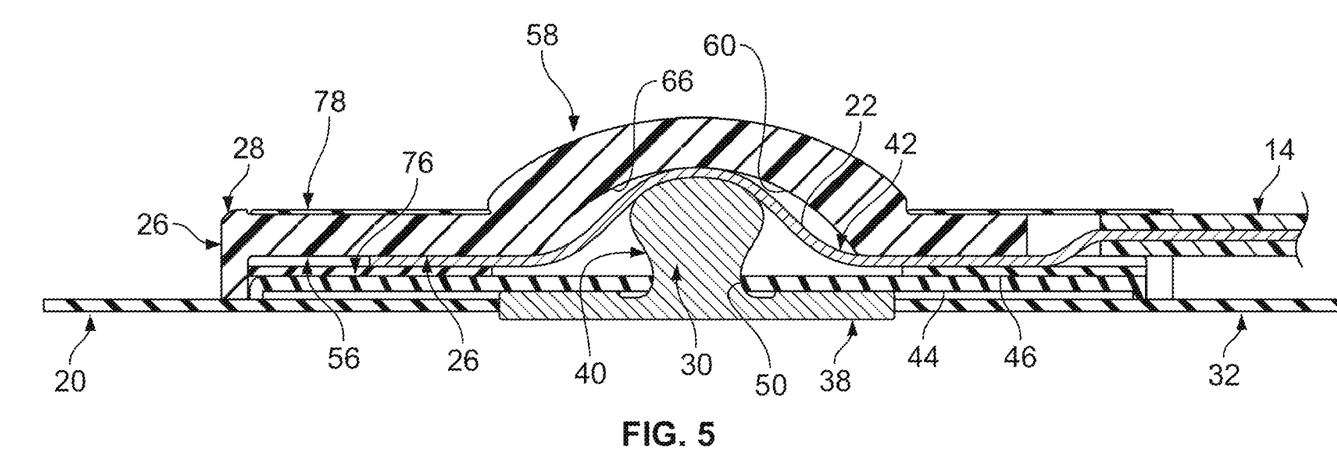
FIG. 5 is a cross sectional view of a portion of the electrode lead assembly shown in FIG. 4 taken along line 5-5 of FIG. 4.

The electrode 20 may be any suitable type of electrode that enables the electrode 20 to function as described herein. In the exemplary embodiment, the electrode 20 is a known ECG electrode. For example, the electrode 20 includes a base 29 that holds an electrical contact 30. The base 29 includes a side portion 32 that engages the patient's body and an opposite side portion 34. The electrical contact 30 extends between opposite end portions 36 and 38. As will be described in more detail below, the end portion 36 electrically connects to the electrical conductor 22 of the electrical lead 14. As can be seen in FIG. 5, in the exemplary embodiment, a portion of the end portion 38 of the electrical contact 30 extends on the side portion 32 of the base 29 and engages the patient's body to form an electrical connection between the electrical contact 30 and the patient's body. In other embodiments, the end portion 38 of the electrical contact 30 engages another electrical contact (not shown) that extends on the side portion 32 of the base 29 for electrical connection to the patient's body. In still other embodiments, the base 29 of the electrode 20 holds an electrically conductive fluid, adhesive, gel, and/or the like (not shown) that is exposed on the side portion 32 of the base 29 for electrical connection with the patient's body; and the end portion 38 of the electrical contact 30 engages the electrically conductive fluid, adhesive, gel, and/or the like to form an electrical connection between the electrical contact 30 and the electrically conductive fluid, adhesive, gel, and/or the like. The end portion 36 of the electrical contact 30 may have any suitable size and/or shape that enables the electrode 20 to function as described herein and/or that enables the connector assembly 28 to function as described herein. In the exemplary embodiment, the end portion 36 of the electrical contact 30 includes a stud 40 such that the electrical contact 30 is a conventional snap-fit contact. As used herein, the term "stud" is intended to mean a protrusion.

The connector assembly 28 connects the distal end portion 18 of the electrical lead 14 to the electrode 20. Specifically, and as will be described below, the connector assembly 28 connects an end portion 42 of the electrical conductor 22 to the electrical contact 30 of the electrode 20. The connector assembly 28 includes the housing 26, a retention plate 44, and a connection member 46. The retention plate 44 includes a body 48 having an opening 50 extending therethrough. The opening 50 has a size and shape that enables the opening 50 to receive the end portion 36 of the electrical contact 30 therethrough. Engagement between the retention plate body 48 adjacent the opening 50 connects the retention plate 44 to the electrical contact 30 such that when the electrical contact end portion 36 is received within opening 50, the retention plate 44 is held on the electrode 20. The opening 50 is not limited to the size and shape described and illustrated in the exemplary embodiment. Rather, the opening 50 may have any suitable size and shape, depending on the size and shape of the electrical contact 30, that enables the opening 50 to receive the electrical contact end portion 36 therethrough and enables the retention plate 44 to be held on the electrode 20. In the exemplary embodiment, the opening 50 has a size and shape that is configured to receive and connect to the stud 40 of a conventional snap-fit electrical contact. Accordingly, in the exemplary embodiment, the opening 50 is sized smaller than an enlarged-diameter portion 52 of the stud 40. However, the portion of the retention plate 44 adjacent the opening 50 is sufficiently resilient such that the size of the opening 50 may deform to allow the enlarged-diameter portion 52 of the stud 40 to be forced through the opening 50. Once the enlarged-diameter portion 52 has passed through the opening 50, the opening 50 returns toward the undeformed size to engage an optional reduced-diameter portion 53 of the stud 40. In the exemplary embodiment, the reduced-diameter portion 53 of the stud 40 is larger than the undeformed size of the opening 50 such that the opening 50 does not return completely to the undeformed size. Alternatively, the reduced diameter portion 53 of the stud 40 is smaller than the undeformed size of the opening 50 such that the opening 50 returns to the undeformed size after deforming to allow the enlarged-diameter portion 52 of the stud 40 to pass therethrough. Turning again to the exemplary embodiment, because the reduced-diameter portion 53 of the stud 40, and thus the size of the opening 50 when the stud 40 has been received therethrough, is smaller than the enlarged-diameter portion 52 of the stud 40, the retention plate 44 remains connected to the electrical contact 30 unless enough force is used to pull the enlarged-diameter portion 52 of the stud 40 back through the opening 50. The retention plate 44 is therefore configured, in the exemplary embodiment, to connect to the electrical contact 30 using a snap-fit connection. It is noted that although in the exemplary embodiment the opening 50 has an approximately circular shape and the stud 40 has an approximately circular cross sectional shape, alternatively the opening 50 and/or the stud 40 have other non-circular shapes.

The housing 26 includes a body 54 having opposite side portions 56 and 58. When the housing 26 is assembled on the electrode 20, the side portion 56 faces the base 29 of the electrode 20. The housing 26 includes a receptacle 60 that extends into the body 54 on the side portion 56 thereof. In the exemplary embodiment, and as best seen in FIG. 3, the receptacle 60 extends into the body 54 between an open end portion 62 and a bottom end portion 64. Specifically, the receptacle 60 is defined by a wall 66 of the body 54. The receptacle 60 has a size and shape that is complimentary to the electrical contact 30 of the electrode 20 such that the receptacle 60 is configured to receive at least a portion of the end portion 36 of the electrical contact 30 therein. As will be described in more detail below, the receptacle 60 is configured such that when the electrical contact 30 is received within the receptacle 60, the receptacle 60 holds at least a portion of the end portion 42 of the electrical conductor 22 within the receptacle 60 between the wall 66 of the receptacle 60 and the end portion 36 of the electrical contact 30 such that the end portion 42 of the electrical conductor 22 is engaged with and electrically connected to the end portion 36 of the electrical contact 30. In an alternative embodiment, the receptacle 60 extends into and completely through the body 54.

The receptacle 60 is not limited to the size and shape described and illustrated in the exemplary embodiment. Rather, the receptacle 60 may have any suitable size and shape, depending on the size and shape of the electrical contact 30, that enables the receptacle 60 to receive at least a portion of the electrical contact 30 and hold at least a portion of the end portion 42 of the electrical conductor 22 within the receptacle 60 in electrical connection with the end portion 36 of the electrical contact 30. In the exemplary embodiment, the receptacle 60 has a size and shape that is configured to receive the stud 40 of a conventional snap-fit electrical contact. It is noted that although the receptacle 60 and the stud 40 have approximately circular cross sectional shapes in the exemplary embodiment, alternatively the receptacle 60 and/or the stud 40 have other non-circular cross-sectional shapes.

The housing 26 may optionally include an opening 68 for receiving a portion of the electrical lead 14 therein, as will be described in more detail below.

As described above, the retention plate 44 connects to the electrical contact 30 of the electrode 20 to hold the retention plate 44 on the electrode 20. The housing 26 is held on the electrode 20 via connection with the retention plate 44. Connection between the housing 26 and the retention plate 44 is made via the connection member 46. The connection member 46 may have any suitable size, shape, configuration, arrangement, structure, means, and/or the like that enables the connection member 46 to connect the housing 26 and the retention plate 44 together. In the exemplary embodiment, the connection member 46 is an adhesive layer. Specifically, the connection member 46 includes a body 70 having a pair of opposite surfaces 72 and 74. Each of the surfaces 72 and 74 includes any suitable adhesive thereon for adhering to the side portion 56 of the housing 26 and a side portion 76 of the retention plate 44, respectively, such as, but not limited to, a self-adhering and/or pressure sensitive adhesive (PSA), and/or the like. Although in the exemplary embodiment the connection member 46 is a separate component from both the housing 26 and the retention plate 44 (at least when not adhered thereto), alternatively the connection member 46 may be one or more components of the housing 26 and/or the retention plate 44, such that the housing 26 and/or the retention plate 44 include the connection member 46. For example, the connection member 46 may be formed from, but is not limited to being formed from, one or more latching components (not shown) of the housing 26 and/or the retention plate 44, one or more interlocking components (not shown) of the housing 26 and/or the retention plate 44, one or more snap-fit connection components (not shown) of the housing 26 and/or the retention plate 44, one or more interference-fit (stiction and/or friction) connection components (not shown) of the housing 26 and/or the retention plate 44, and/or the like.

The connector assembly 28 may optionally include an adhesive layer 78 that covers at least a portion of the housing 26. Specifically, the adhesive layer 78 includes a pair of opposite surfaces 80 and 82. The surface 82 includes any suitable adhesive for adhering the adhesive layer 78 to the housing 26, such as, but not limited to, a self-adhering and/or pressure sensitive adhesive (PSA), and/or the like. Optionally, the adhesive layer 78 may also cover and adhere to at least a portion of the side portion 34 of the electrode base 29 to facilitate holding the housing 26 on the electrode 20 and/or to facilitate providing strain relief to the electrical lead 14. The adhesive layer 78 may optionally include indicia 84. The indicia 84 may indicate any information, such as, but not limited to, a location on the patient's body where the electrode is desired to be placed and/or the like. In the exemplary embodiment, the adhesive layer 78 includes an optional opening 86 that receives a portion of the body 54 of the housing 26.

Figure 4:
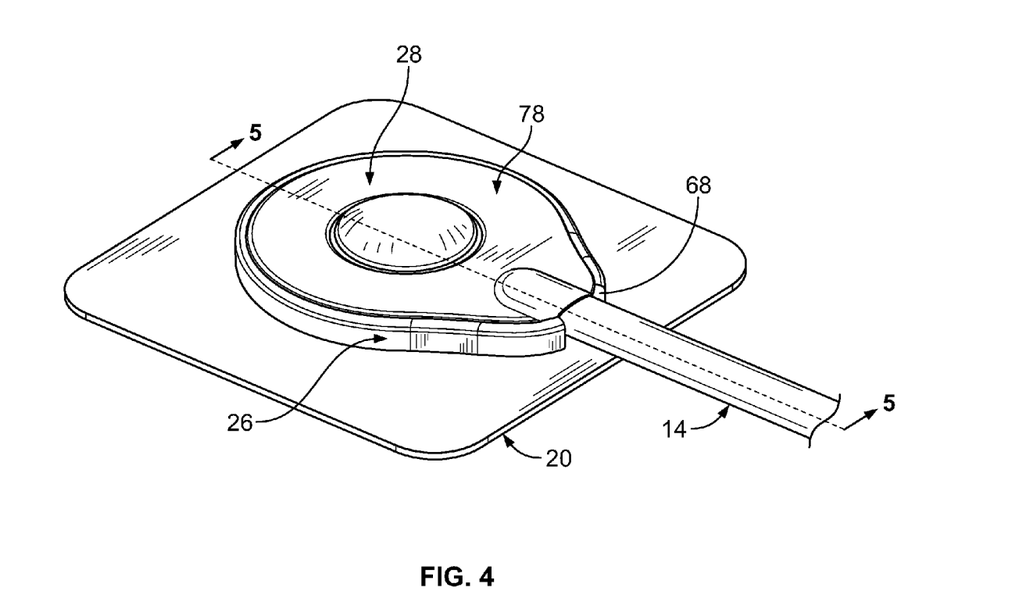
FIG. 4 is a perspective view of the electrode lead assembly shown in FIG. 2 illustrating the electrode lead assembly in an assembled state.

Referring now to FIGS. 4 and 5, to connect the electrical lead 14 to the electrode 20, the end portion 42 of the electrical conductor 22 is positioned at least partially within the receptacle 60 of the housing 26. The connection member 46 is positioned between the housing 26 and the retention plate 44. The housing 26 and the retention plate 44 are connected together by adhering the connection member 46 to the side portion 56 of the housing 26 and the side portion 76 of the retention plate 44, with at least a portion of the end portion 42 of the electrical conductor 22 being held within the receptacle 60. The connector assembly 28 is positioned over the stud 40 of the electrode 20 and the stud 40 is inserted through the opening 50 within the retention plate 44 and into the receptacle 60 of the housing 26. A portion of the end portion 42 of the electrical conductor 22 thereby extends between, and is engaged with, the wall 66 of the receptacle 60 and the stud 40 of the electrode 20. The engagement between the stud 40 and the end portion 42 of the electrical conductor 22 forms an electrical connection between the electrode 20 and the electrical conductor 22. The retention plate 44 is held on the electrode 20 via the snap-fit connection between the retention plate 44 and the stud 40, while the connection member 46 holds the housing 26 on the electrode 20 by connecting the housing 26 to the retention plate 44. In the exemplary embodiment, the complimentary size and shape of the receptacle 60 relative to the stud 40 causes a portion of the end portion 42 of the electrical conductor 22 to at least partially conform approximately to the contour of the stud 40 when assembled as described and illustrated herein. The opening 68 within the housing 26 may receive a portion of the electrical lead 14 therein to facilitate providing strain relief to the electrical lead 14.

Although the connector assembly 28 and the electrical lead 14 are described herein as being assembled together prior to connecting the electrical lead 14 to the electrode 20, the connector assembly 28 and the electrical lead 14 may alternatively be assembled as the electrical lead 14 is connected to the electrode 20. For example, the retention plate 44 may first be connected to the stud 40 of the electrode 20. The connection member 46 may then be adhered to the side portion 76 of the retention plate 44, and the end portion 42 of the electrical conductor 22 may then be positioned over the stud 40. The housing 26 may then be connected to the retention plate 44 via the connection member 46, with at least a portion of the end portion 42 of the electrical conductor 22 being held within the receptacle 60 between, and in engagement with, the stud 40 and the wall 66.

The optional adhesive layer 78 may be attached to the side portion 58 of the housing 26 at any time before, during, or after assembly of the connector assembly 28 and the electrical lead 14 and/or connection of the electrical lead 14 to the electrode 20.

The electrical leads 14 and the connector assembly 28 may be sold or supplied to healthcare providers, or an intermediate party, as part of the electrode lead set 10 or a single electrode lead assembly 12, whether supplied or sold as assembled and/or connected to the electrodes 20. Alternatively, the electrical leads 14 and the connector assembly 28 may be supplied or sold to healthcare providers, or an intermediate party, without the electrodes 20 (whether the electrical lead 14 is assembled with the connector assembly 28), and the healthcare provider, or the intermediary party, may supply and connect the electrodes 20 to the electrical leads 14, for example immediately prior to application of the electrodes 20 to the patient's body. Moreover, the connector assembly 28 may be sold or supplied to healthcare providers, or an intermediate party, by themselves and the healthcare provider, or the intermediary party, may supply the electrical leads 14 and the electrodes 20. In some embodiments, the electrical leads 14 and/or the connector assemblies 28 may be reusable with different electrodes 20, for example by removing the connector assembly 28 to disconnect the electrical lead 14 from an electrode 20 and connecting the electrical lead 14 to another electrode 20 using the connector assembly 28. In other embodiments, once an electrical lead 14 is connected to an electrode 20, the electrical lead 14 and/or the connector assembly 28 is not intended to be reusable with another electrode.

Figure 6:
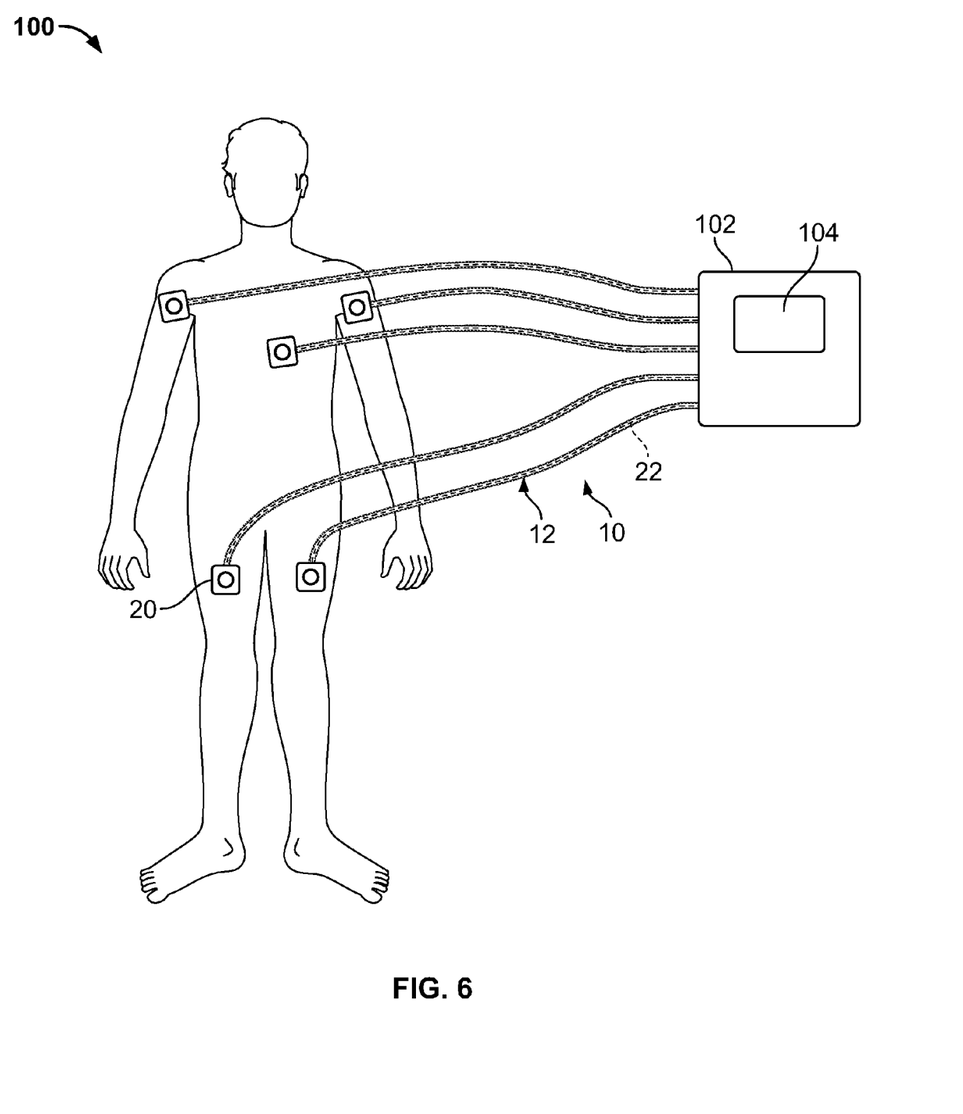

FIG. 6 is a schematic diagram of an exemplary embodiment of an ECG system 100 that the electrode lead set 10 may be, but is not limited to being, used with. The ECG system 100 includes the electrode lead set 10 and an ECG monitoring device 102. The electrode lead set 10 is connected to the ECG monitoring device 102 such that the electrical conductors 22 are electrically connected to one or more corresponding circuits (not shown) of the ECG monitoring device 102. Each electrode lead assembly 12 may directly connect to the ECG monitoring device 102, or may connect to the device 102 using any suitable extension (not shown). The ECG monitoring device 102 may be any suitable processing device that is capable of performing signal processing and computational operations to convert the raw electrical signals from the electrodes 20 into meaningful ECG information that may optionally be displayed on a monitor 104, printed for review by a physician, and/or the like.

In operation, each electrode lead assembly 12 is manipulated to place the corresponding electrode 20 at a desired location on the patient's body. In the exemplary embodiment of FIG. 6, some of the electrodes 20 are placed on a chest region of the patient's body adjacent the heart, and others of the electrodes 20 are placed on the patient's body at the prescribed limb locations RA, LA, RL, and LL of the AHA. However, the ECG system 100 is not limited to using five electrodes 20, is not limited to the specific locations shown, and each of the electrodes 20 is not limited to being placed at the corresponding location shown. Rather, the ECG system 100 may use any number of electrodes 20 each located at any suitable location on the patient's body for performing ECG measurements. The particular locations shown in FIG. 6 as well as which electrode 20 of the set 10 is placed at such locations is meant as exemplary only. For example, the set 10 may include more or less electrode lead assemblies 12 and electrodes 20 than five, and/or the system 100 may use more than one electrode lead set (e.g., a set for the chest region and a different set for the limbs). Different locations (e.g., different locations on the chest region and/or the limbs) than those shown may be used in addition or alternative to the locations shown.

Once all of the electrodes 20 are placed at the desired locations on the patient's body, the ECG monitoring device 102 receives electrical signals of the electrodes 20 and converts the signals into meaningful ECG information.

In an alternative embodiment, the electrical conductors 22 are electrically connected to a hand-held system monitor (not shown). In another alternative embodiment, the electrical conductors 22 are electrically connected to a wireless transceiver (not shown) such that the ECG signals are transmitted to the hand-held system monitor and/or the ECG monitoring device 102 via a wireless connection.

Figure 7:
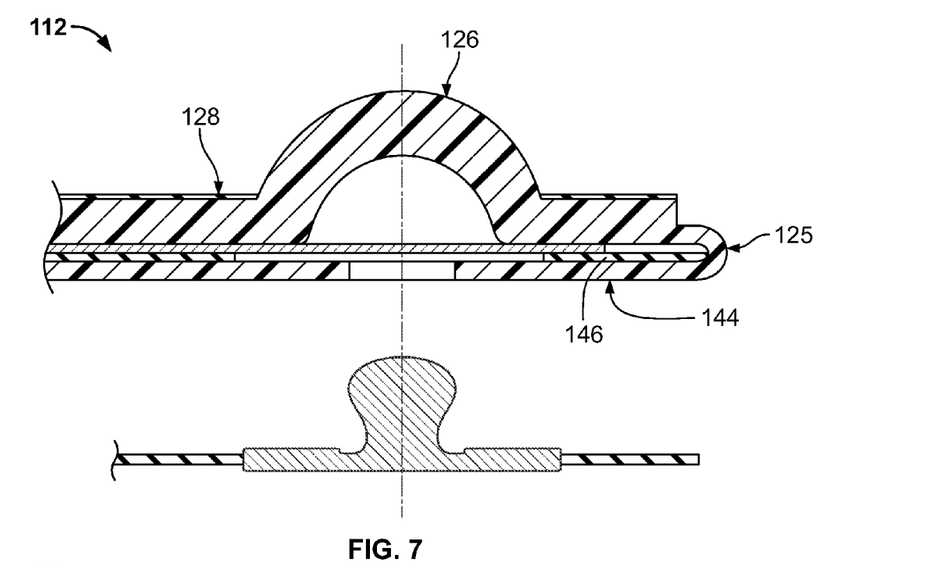
FIG. 7 is a partially exploded cross sectional view of a portion of an exemplary alternative embodiment of an electrode lead assembly.

Although the housing 26 and the retention plate 44 are shown as being separate components that are not connected together until the connector assembly 28 is assembled, alternatively the housing 26 and the retention plate 44 may be connected together when the connector assembly 28 is not assembled (whether or not the housing 26 and the retention plate 44 are formed integrally). For example, FIG. 7 is a partially exploded cross sectional view of a portion of an exemplary alternative embodiment of an electrode lead assembly 112. The electrode lead assembly 112 includes a connector assembly 128 that includes a housing 126 and a retention plate 144. The housing 126 and the retention plate 144 are connected together by a hinge 125. The hinge 125 may be any suitable type of hinge, such as, but not limited to, a living hinge and/or the like. A connection member 146 having any suitable size, shape, configuration, arrangement, structure, means, and/or the like connects the housing 126 and the retention plate 144 together. A combination of an electrical lead 114 and the connector assembly 128 may be referred to herein as an "electrical lead assembly".

Figure 8:
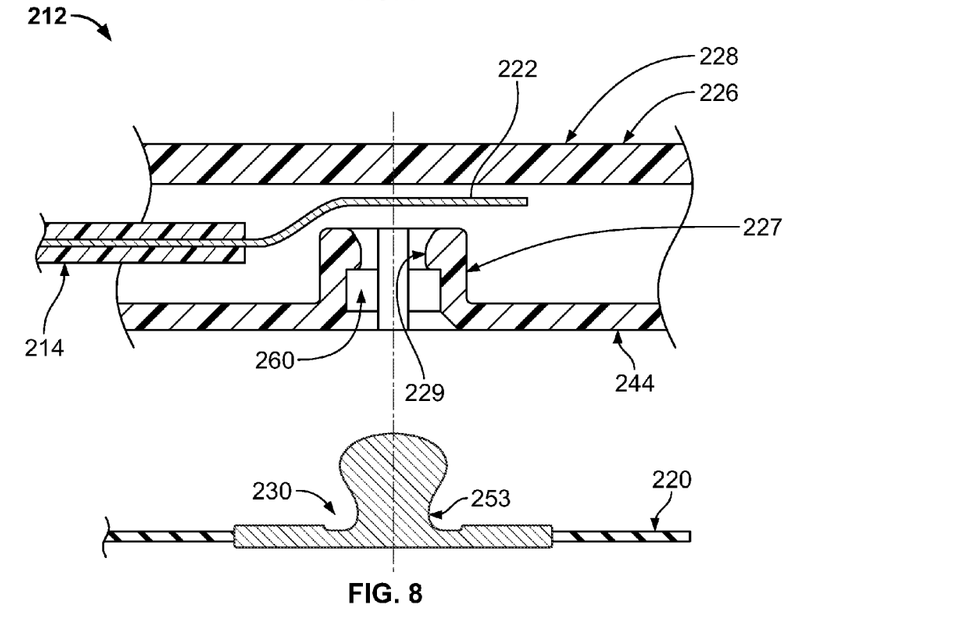
FIG. 8 is a partially exploded cross sectional view of a portion of another exemplary alternative embodiment of an electrode lead assembly.

Referring again to the exemplary embodiment of FIGS. 1-6, although the receptacle 60 is defined by the housing 26, the receptacle 60 may alternatively be defined by the retention plate 44. For example, FIG. 8 is a partially exploded cross sectional view of a portion of an exemplary alternative embodiment of an electrode lead assembly 212. The electrode lead assembly 212 includes an electrical lead 214, an electrode 220, and a connector assembly 228. The electrode 220 includes an electrical contact 230 and the electrical lead 214 includes an electrical conductor 222. The connector assembly 228 includes a housing 226 and a retention plate 244. The retention plate 244 includes a plurality of latching fingers 227 that are arranged to define a receptacle 260. In the exemplary embodiment, the receptacle 260 receives the electrical contact 230 therein in a snap-fit connection. Specifically, in the exemplary embodiment extensions 229 of the latching fingers 227 engage a reduced diameter portion 253 of the electrical contact 230 to hold the electrical contact 230 within the receptacle 260. The electrical conductor 222 is held between, and in engagement with, the electrical contact 230 and the housing 226 such that the electrical contact 230 is electrically connected to the electrical conductor 222. A connection member (not shown) having any suitable size, shape, configuration, arrangement, structure, means, and/or the like connects the housing 226 and the retention plate 244 together. A combination of an electrical lead 214 and the connector assembly 228 may be referred to herein as an "electrical lead assembly".

Figure 9:
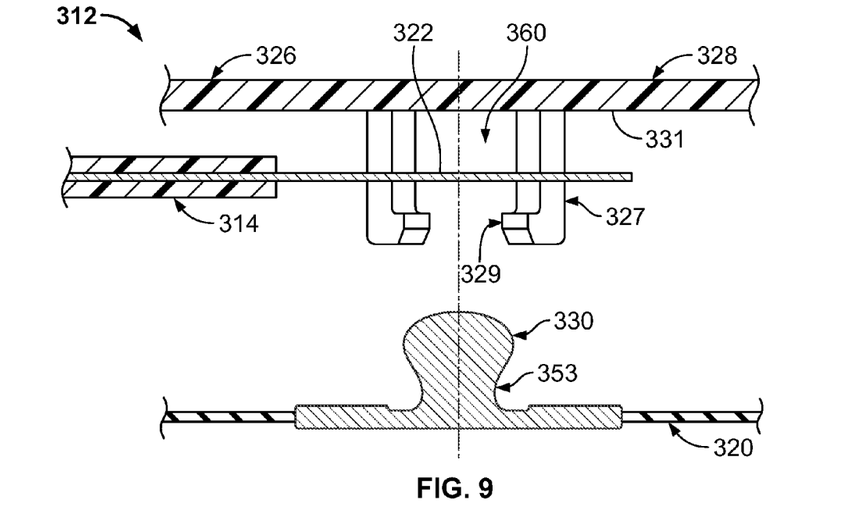
FIG. 9 is a partially exploded cross sectional view of a portion of another exemplary alternative embodiment of an electrode lead assembly.
Figure 10:
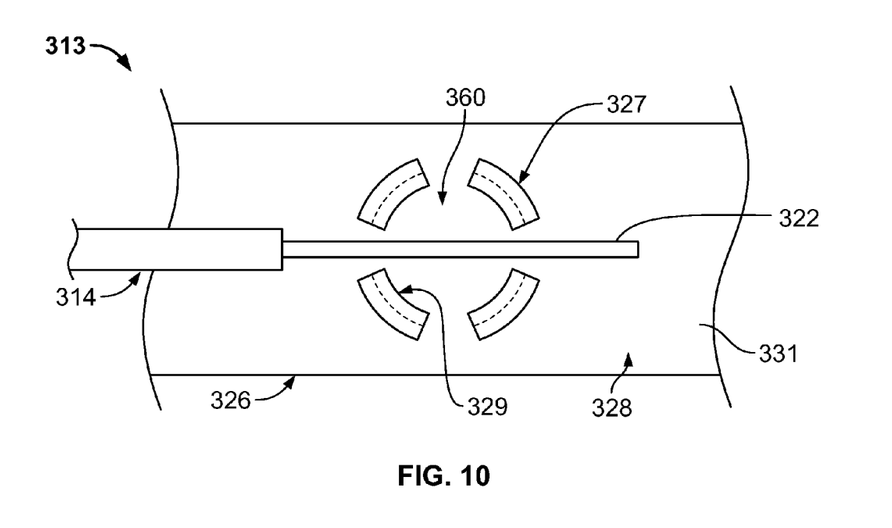
FIG. 10 is a bottom plan view of an exemplary embodiment of a portion of an electrical lead assembly of the electrode lead assembly shown in FIG. 9.

FIG. 9 is a partially exploded cross sectional view of a portion of another exemplary alternative embodiment of an electrode lead assembly 312. FIG. 10 is a bottom plan view of an exemplary embodiment of a portion of an electrical lead assembly 313 of the electrode lead assembly 312 shown in FIG. 9. The electrode lead assembly 312 includes an electrical lead 314, an electrode 320, and a connector assembly 328. The electrode 320 includes an electrical contact 330 and the electrical lead 314 includes an electrical conductor 322. The connector assembly 328 includes a housing 326, but does not include a retention plate. The housing 326 includes a plurality of latching fingers 327 that are arranged to define a receptacle 360. In the exemplary embodiment, the receptacle 360 receives the electrical contact 330 therein in a snap-fit connection. Specifically, in the exemplary embodiment extensions 329 of the latching fingers 327 engage a reduced diameter portion 353 of the electrical contact 330 to hold the electrical contact 330 within the receptacle 360. The electrical conductor 322 is held between, and in engagement with, the electrical contact 330 and a wall 331 of the housing 326 such that the electrical contact 330 is electrically connected to the electrical conductor 322. A combination of an electrical lead 314 and the connector assembly 328 may be referred to herein as an "electrical lead assembly".

Figure 11:
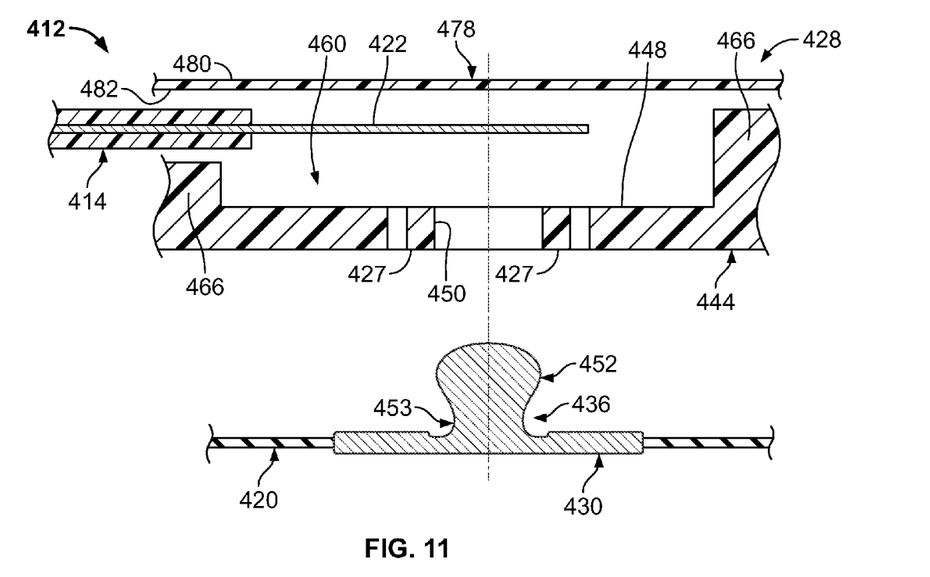
FIG. 11 is a partially exploded cross sectional view of a portion of another exemplary alternative embodiment of an electrode lead assembly.
Figure 12:
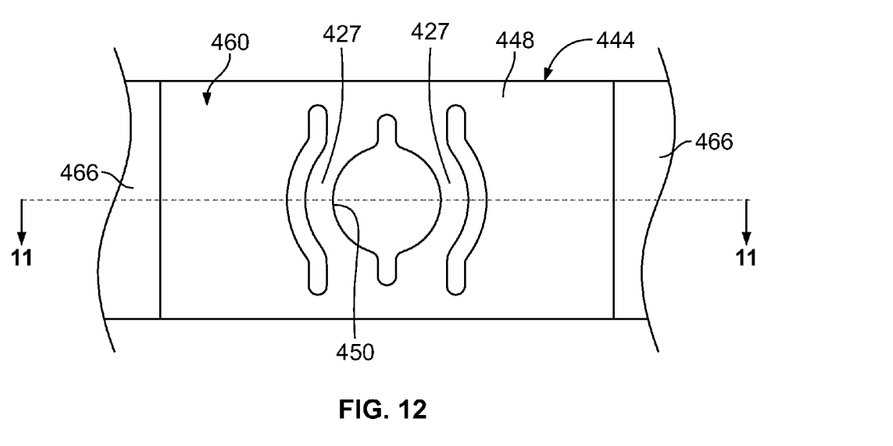
FIG. 12 is a top plan view of an exemplary embodiment of a portion of a retention plate of the electrode lead assembly shown in FIG. 11.

FIG. 11 is a partially exploded cross sectional view of a portion of another exemplary alternative embodiment of an electrode lead assembly 412. FIG. 12 is a top plan view of an exemplary embodiment of a portion of a retention plate 444 of the electrode lead assembly 412. The electrode lead assembly 412 includes an electrical lead 414, an electrode 420, and a connector assembly 428. The electrode 420 includes an electrical contact 430 and the electrical lead 414 includes an electrical conductor 422. The connector assembly 428 includes the retention plate 444 and a cover sheet 478, but does not include a housing. The retention plate 444 includes a body 448 having an opening 450 extending therethrough. The opening 450 has a size and shape that enables the opening 450 to receive an end portion 436 of the electrical contact 430 therethrough. In the exemplary embodiment, the opening 450 is defined by a pair of flexible beams 427 and is sized smaller than an enlarged-diameter portion 452 of the electrical contact 430. The beams 427 are sufficiently resilient such that the size of the opening 450 may deform to allow the enlarged-diameter portion 452 of the electrical contact 430 to be forced through the opening 450. Once the enlarged-diameter portion 452 has passed through the opening 450, the beams 427, and thereby the opening 450, return toward the undeformed size to engage a reduced-diameter portion 453 of the electrical contact 430, such that in the exemplary embodiment the body 448 of the retention plate 444 connects to the electrical contact 430 in a snap-fit connection.

The body 448 of the retention plate 444 includes one or more walls 466 that are arranged to define a receptacle 460. The receptacle 460 receives at least a portion of the end portion 436 of the electrical contact 430 therein. The electrical conductor 422 is held between, and in engagement with, the electrical contact 430 and the cover sheet 478, which holds a portion of the electrical lead 414 on the retention plate 444. The cover sheet 478 includes a pair of opposite surfaces 480 and 482. In the exemplary embodiment, the surface 482 includes any suitable adhesive for adhering the cover sheet 478 to the retention plate 444, such as, but not limited to, a self-adhering and/or pressure sensitive adhesive (PSA), and/or the like. The cover sheet 478 may optionally include indicia (not shown). The indicia may indicate any information, such as, but not limited to, a location on the patient's body where the electrode is desired to be placed and/or the like. A combination of an electrical lead 414 and the connector assembly 428 may be referred to herein as an "electrical lead assembly".

Figure 13:
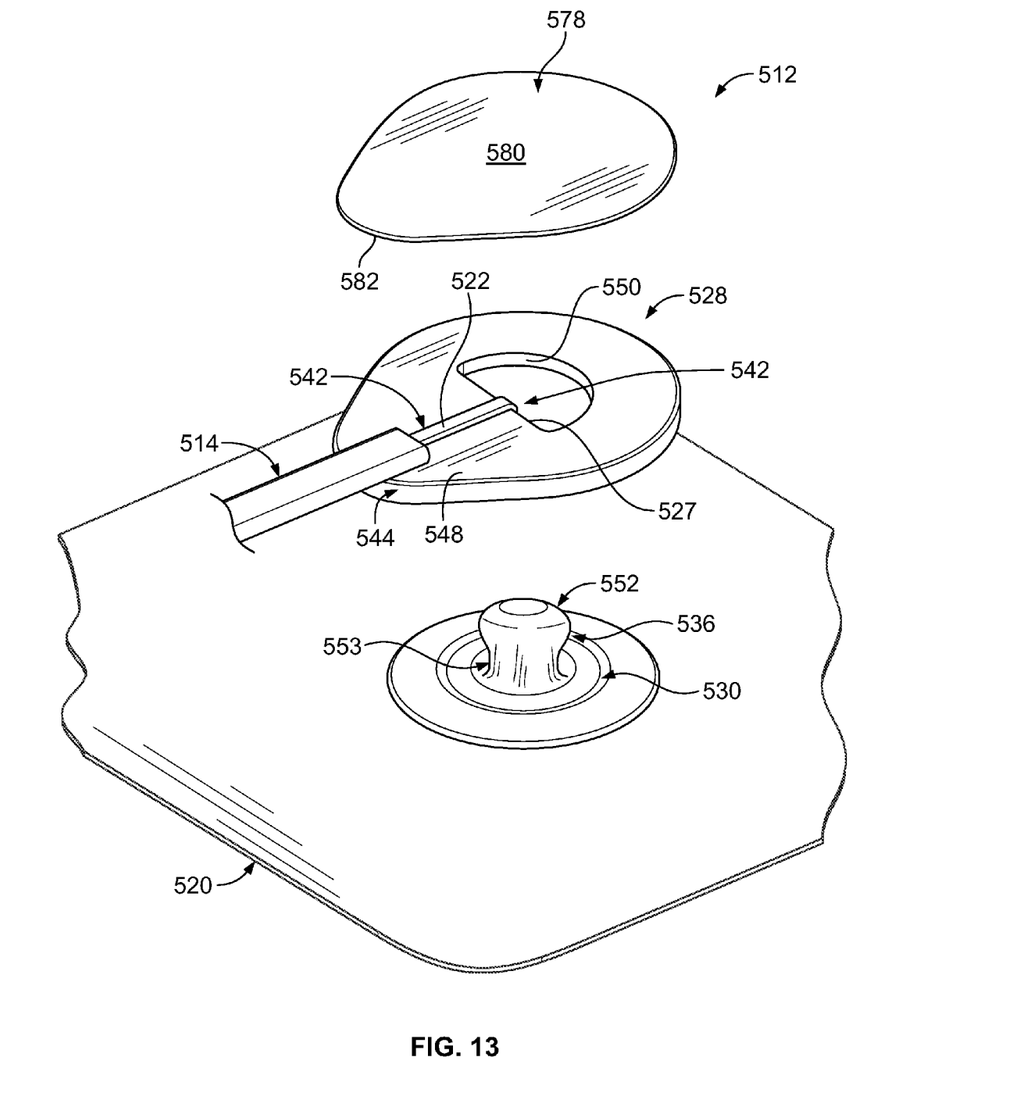
FIG. 13 is a partially exploded perspective view of a portion of another exemplary alternative embodiment of an electrode lead assembly.

FIG. 13 is a partially exploded perspective view of a portion of another exemplary alternative embodiment of an electrode lead assembly 512. The electrode lead assembly 512 includes an electrical lead 514, an electrode 520, and a connector assembly 528. The electrode 520 includes an electrical contact 530 and the electrical lead 514 includes an electrical conductor 522. The connector assembly 528 includes a retention plate 544 and a cover sheet 578, but does not include a housing. The retention plate 544 includes a body 548 having an opening 550 extending therethrough. The opening 550 has a size and shape that enables the opening 550 to receive an end portion 536 of the electrical contact 530 therethrough. In the exemplary embodiment, the opening 550 is sized smaller than an enlarged-diameter portion 552 of the electrical contact 530. The portion of the retention plate body 548 adjacent the opening 550 is sufficiently resilient such that the size of the opening 550 may deform to allow the enlarged-diameter portion 552 of the electrical contact 530 to be forced through the opening 550. Once the enlarged-diameter portion 552 has passed through the opening 550, the opening 550 returns toward the undeformed size to engage a reduced-diameter portion 553 of the electrical contact 530, such that in the exemplary embodiment the body 548 of the retention plate 544 connects to the electrical contact 530 in a snap-fit connection.

A portion of an end portion 542 of the electrical conductor 522 is held between, and in engagement with, the electrical contact 530 and a wall 527 of the retention plate body 548 that defines the opening 550. The cover sheet 578 holds a portion of the electrical lead 514 on the retention plate 544. The cover sheet 578 includes a pair of opposite surfaces 580 and 582. In the exemplary embodiment, the surface 582 includes any suitable adhesive for adhering the cover sheet 578 to the retention plate 544, such as, but not limited to, a self-adhering and/or pressure sensitive adhesive (PSA), and/or the like. The cover sheet 578 may optionally include indicia (not shown). The indicia may indicate any information, such as, but not limited to, a location on the patient's body where the electrode is desired to be placed and/or the like. A combination of an electrical lead 514 and the connector assembly 528 may be referred to herein as an "electrical lead assembly".

Figure 14:
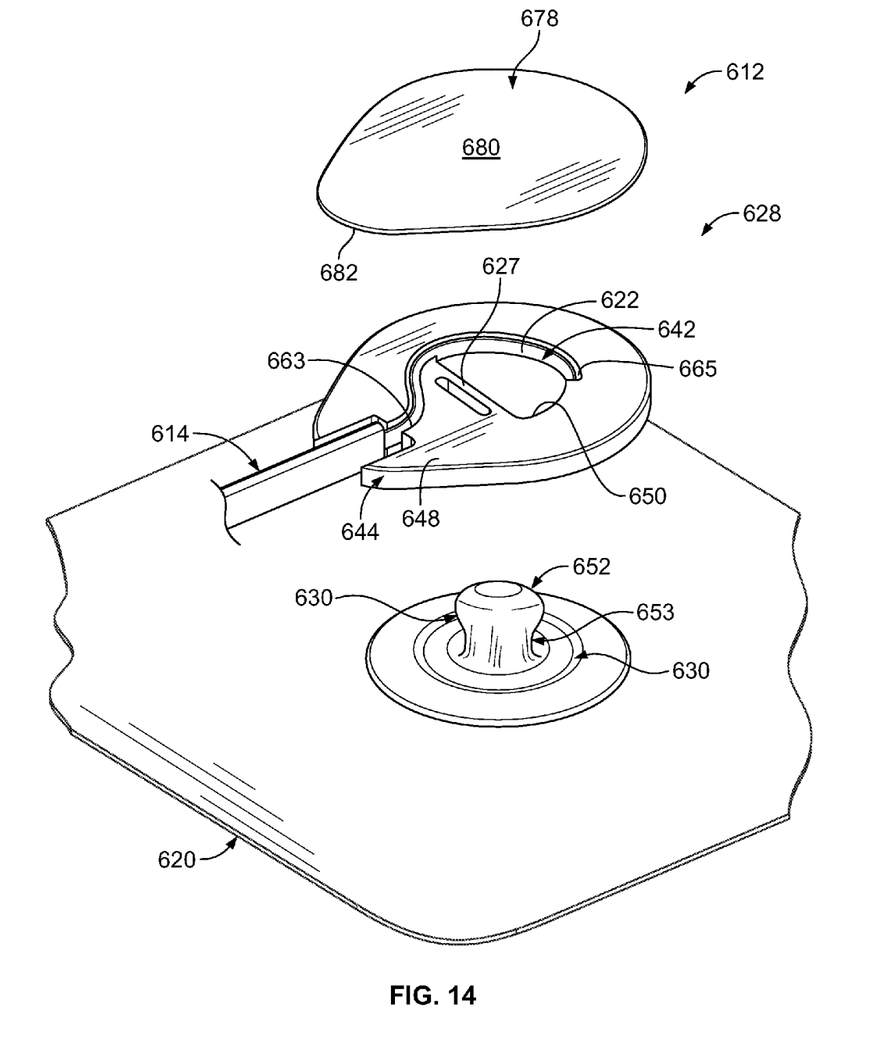
FIG. 14 is a partially exploded perspective view of a portion of another exemplary alternative embodiment of an electrode lead assembly.

FIG. 14 is a partially exploded perspective view of a portion of another exemplary alternative embodiment of an electrode lead assembly 612. The electrode lead assembly 612 includes an electrical lead 614, an electrode 620, and a connector assembly 628. The electrode 620 includes an electrical contact 630 and the electrical lead 614 includes an electrical conductor 622. The connector assembly 628 includes a retention plate 644 and an optional cover sheet 678, but does not include a housing. The retention plate 644 includes a body 648 having an opening 650 extending therethrough. The opening 650 has a size and shape that enables the opening 650 to receive an end portion 636 of the electrical contact 630 therethrough. In the exemplary embodiment, the opening 650 is sized smaller than an enlarged-diameter portion 652 of the electrical contact 630. The portion of the retention plate body 648 adjacent the opening 650 is sufficiently resilient such that the size of the opening 650 may deform to allow the enlarged-diameter portion 652 of the electrical contact 630 to be forced through the opening 650. For example, in the exemplary embodiment a portion of the retention plate body 648 that defines a portion of the opening 650 is provided as a flexible beam 627. Once the enlarged-diameter portion 652 has passed through the opening 650, the beam 627, and thereby the opening 650, returns toward the undeformed size to engage a reduced-diameter portion 653 of the electrical contact 630, such that in the exemplary embodiment the body 648 of the retention plate 644 connects to the electrical contact 630 in a snap-fit connection.

The body 648 of the retention plate 644 includes a channel 663 that holds an end portion 642 of the electrical conductor 622 therein. A portion of the end portion 642 is held between, and in engagement with, the electrical contact 630 and a wall 665 of the retention plate body 648 that defines the opening 650. The optional cover sheet 678 covers a portion of the electrical lead 614 and the retention plate 644. The optional cover sheet 678 includes a pair of opposite surfaces 680 and 682. In the exemplary embodiment, the surface 682 includes any suitable adhesive for adhering the optional cover sheet 678 to the retention plate 644, such as, but not limited to, a self-adhering and/or pressure sensitive adhesive (PSA), and/or the like. The optional cover sheet 678 may optionally include indicia (not shown). The indicia may indicate any information, such as, but not limited to, a location on the patient's body where the electrode is desired to be placed and/or the like. A combination of an electrical lead 614 and the connector assembly 628 may be referred to herein as an "electrical lead assembly".

The embodiments thus described provide an electrical lead that may be less costly and/or more easily manufactured, assembled, and/or connected to an electrode than at least some known electrical leads.

Although the embodiments described and illustrated herein are described and illustrated herein for use with an ECG system, the embodiments described and illustrated herein are not limited to being used with ECG systems for taking ECG measurements. Rather, the embodiments described and illustrated herein may be used with any system for measuring any physiologic information or performing any physiologic procedure, such as, but not limited to, for performing an electroencephalogram (EEG) procedure, for performing muscle and/or nerve stimulation and/or therapy, and/or for performing an electrophysiologic procedure. In some embodiments, the embodiments described and illustrated herein may be a hybrid that may be used to perform a plurality of different types of physiologic measurements and/or procedures.

Exemplary embodiments are described and/or illustrated herein in detail. The embodiments are not limited to the specific embodiments described herein, but rather, components and/or steps of each embodiment may be utilized independently and separately from other components and/or steps described herein. Each component, and/or each step of one embodiment, can also be used in combination with other components and/or steps of other embodiments. When introducing elements/components/etc. described and/or illustrated herein, the articles "a", "an", "the", "said", and "at least one" are intended to mean that there are one or more of the element(s)/component(s)/etc. The terms "comprising", "including" and "having" are intended to be inclusive and mean that there may be additional element(s)/component(s)/etc. other than the listed element(s)/component(s)/etc. Moreover, the terms "first," "second," and "third," etc. in the claims are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

While the subject matter described and illustrated herein has been described in terms of various specific embodiments, those skilled in the art will recognize that the subject matter described and illustrated herein can be practiced with modification within the spirit and scope of the claims.

What is claimed is:

1. A connector assembly for connecting an electrical lead to an electrical contact of an electrode, said connector assembly comprising:
    a retention plate having an opening configured to receive the electrical contact of the electrode therethrough such that the retention plate is held on the electrode;
    a housing including a body and a receptacle extending into the body, the receptacle being defined by a wall of the body and comprising a size and shape that is complimentarily to the electrical contact of the electrode such that the receptacle is configured to receive at least a portion of the electrical contact therein, wherein the receptacle is configured such that when the electrical contact is received within the receptacle, the receptacle is configured to hold a portion of the electrical lead within the receptacle between the electrical contact and the wall of the body of the housing such that the electrical lead is engaged with and electrically connected to the electrical contact; and
    a connection member configured to hold the housing on the retention plate.

2. The connector assembly according to claim 1, wherein the connection member comprises an adhesive layer configured to be positioned between and in engagement with the housing and the retention plate.

3. The connector assembly according to claim 1, wherein at least one of the housing and the retention plate comprises the connection member.

4. The connector assembly according to claim 1, wherein the opening of the retention plate is sized smaller than a portion of the electrical contact.

5. The connector assembly according to claim 1, wherein the retention plate is configured to connect to the electrical contact using a snap-fit connection.

6. The connector assembly according to claim 1, further comprising an adhesive layer covering at least a portion of the housing.

7. The connector assembly according to claim 1, further comprising an adhesive layer covering at least a portion of the housing, wherein the adhesive layer comprises indicia.

8. The connector assembly according to claim 1, wherein the retention plate is configured to be positioned between the housing and a body of the electrode when the connector assembly connects the electrical lead to the electrical contact of the electrode.

9. An electrical lead assembly for connection to an electrical contact of an electrode, said electrical lead assembly comprising:
    a retention plate having an opening configured to receive the electrical contact of the electrode therethrough such that the retention plate is held on the electrode;
    a housing including a body and a receptacle extending into the body, the receptacle being defined by a wall of the body and being configured to receive at least a portion of the electrical contact therein;
    an electrical lead having an end portion; and
    a connection member holding the housing on the retention plate, wherein the receptacle is configured such that when the electrical contact is received within the opening of the retention plate and within the receptacle, at least a portion of the end portion of the electrical lead is held within the receptacle between the electrical contact of the electrode and the wall of the body of the housing such that the electrical lead is engaged with and electrically connected to the electrical contact.

10. The electrical lead assembly according to claim 9, wherein the connection member comprises an adhesive layer positioned between and in engagement with the housing and the retention plate.

11. The electrical lead assembly according to claim 9, wherein at least one of the housing and the retention plate comprises the connection member.

12. The electrical lead assembly according to claim 9, wherein the opening of the retention plate is sized smaller than a portion of the electrical contact.

13. The electrical lead assembly according to claim 9, wherein the retention plate is configured to connect to the electrical contact using a snap-fit connection.

14. The electrical lead assembly according to claim 9, further comprising an adhesive layer covering at least a portion of the housing.

15. The electrical lead assembly according to claim 9, further comprising an adhesive layer covering at least a portion of the housing, wherein the adhesive layer comprises indicia.

16. The electrical lead assembly according to claim 9, wherein the retention plate is positioned between the housing and a body of the electrode when the connector assembly connects the electrical lead to the electrical contact of the electrode.

17. The electrical lead assembly according to claim 9, wherein the electrical lead comprises one of an approximately cylindrical wire and an approximately planar shape.

18. The electrical lead assembly according to claim 9, wherein the end portion of the electrical lead is a distal end portion and the electrical lead extends between the distal end portion and a proximal end portion that is configured to be electrically connected to an electronic device.

19. The electrical lead assembly according to claim 9, wherein the electrical lead assembly is an electrocardiograph (ECG) electrical lead assembly.

20. An electrode lead assembly comprising:

an electrode including an electrical contact;

a retention plate held on the electrode, the retention plate including an opening having the electrical contact of the electrode received therethrough;

a housing including a body and a receptacle extending into the body, at least a portion of the electrical contact being received into the receptacle;

an electrical lead having an end portion, at least a portion of the end portion of the electrical lead being held within the receptacle between the electrical contact of the electrode and a wall of the body of the housing such that the electrical lead is engaged with and electrically connected to the electrical contact; and a connection member holding the housing on the retention plate.

* * * * *